United States Patent [19]

Camberlin et al.

[11] Patent Number: 5,324,827

[45] Date of Patent: Jun. 28, 1994

[54] OPTIONALLY ORIENTED, MONOMERIC AND POLYMERIC NONLINEARLY OPTICALLY ACTIVE MATERIALS AND DERIVATIVES THEREOF

[75] Inventors: Yves Camberlin, Caluire; Gerard Mignani, Lyons; Remi Meyrueix, Lyons; Gilles Tapolsky, Lyons, all of France

[73] Assignee: Flamel Technologies, Venissieux Cedex, France

[21] Appl. No.: 118,286

[22] Filed: Sep. 9, 1993

Related U.S. Application Data

[63] Continuation of Ser. No. 766,514, Sep. 27, 1991, abandoned.

[30] Foreign Application Priority Data

Sep. 28, 1990 [FR] France ............................ 90 11956

[51] Int. Cl.$^5$ ............................................ C07C 245/06
[52] U.S. Cl. .................................... 534/854; 534/838; 534/886; 534/885
[58] Field of Search ............................. 534/854, 838

[56] References Cited

U.S. PATENT DOCUMENTS

| | | | |
|---|---|---|---|
| 3,503,954 | 3/1970 | Gies | 534/854 |
| 4,448,719 | 5/1984 | Schwander | 534/854 |
| 4,552,951 | 11/1985 | Gourley | 534/854 |
| 4,757,130 | 7/1988 | DeMartino . | |

OTHER PUBLICATIONS

New Heat-Resistant Polymers Derived from Azomethine Bismaleimides and Maleimide-Terminated Azomethine Prepolymers, *Journal of Polymer Science: Part A: Polymer Chemistry*, vol. 27, 3465-3479 (John Wiley & Sons, Inc., 1989).

*Primary Examiner*—Marianne M. Cintins
*Assistant Examiner*—John Peabody
*Attorney, Agent, or Firm*—Burns, Doane, Swecker & Mathis

[57] ABSTRACT

Nonlinearly optically active monomer species comprising at least two carbon-carbon activated double bonds, i.e., the polymerization of which is facilitated by the presence of an electron attracting function, and a noncentrosymmetric system of pi ($\pi$) conjugated bonds bearing at least one electron attracting group on one terminal thereof and at least one electron donor group on the other terminal, are readily (co)polymerized and optionally oriented and crosslinked into shaped articles well adopted for the manufacture of a variety of electrooptical devices; such monomer species can have, for example, the following structural formula (I):

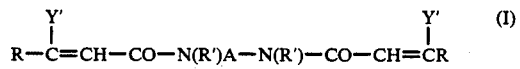

8 Claims, No Drawings

OPTIONALLY ORIENTED, MONOMERIC AND POLYMERIC NONLINEARLY OPTICALLY ACTIVE MATERIALS AND DERIVATIVES THEREOF

This application is a continuation of application Ser. No. 07/766,514, filed Sep. 27, 1991 now abandoned.

BACKGROUND OF THE INVENTION

1. Field of the Invention

The present invention relates to novel chemical compounds and to the production of nonlinearly optically active organic materials therefrom.

This invention especially relates to high molecular weight organic polymeric materials having a high concentration in recurring structural units that are hyperpolarizable or nonlinearly optically active.

2. Description of the Prior Art

Numerous materials exhibiting nonlinear optical activity are known to this art. Among such materials, the organics typically comprise a polymerizable matrix, in which a hyperpolarizable organic compound is dissolved or incorporated. However, these materials present certain disadvantages, principally by reason of the solubility and compatibility of the organic compound in the matrix.

Furthermore, in such systems, also designated "guest/host" systems, a certain mobility of the hyperpolarizable compounds always remains. Thus, the orientation of the molecules effected by the exposure of the material to an electric field will disappear upon aging, causing a reduction in the nonlinear optical activity thereof.

Polycondensed organic materials containing hyperpolarizable groups grafted onto the principal backbone chain of the polymer via hydrocarbon moieties of varying length, are also known to this art.

As in the aforementioned systems of the "guest/host" type, there remains a certain residual mobility of the hyperpolarizable species, ultimately resulting in a reduction in the nonlinear optical activity upon aging of the material.

Lastly, high molecular weight organic materials are also known to this art, prepared by the polycondensation of a monomer comprising reactive functions borne by a hyperpolarizable group, with a monomer comprising conjugated functions.

Thus, if the reactive functions are hydroxyl radicals, the conjugated monomer may be a diisocyanate.

In such materials, the hyperpolarizable group constitutes a portion of the principal backbone chain or skeleton of the polymer. Consequently, the residual mobility of these groups is significantly reduced, as it requires a mobility of the polymer chain. However, the latter is not zero and it is observed that following the orientation stage under the influence of an electric field, there is a slow return towards disorder, thereby resulting in a gradual loss of the nonlinear (square) optical activity.

For example, published Japanese application No. 88/175,837 describes compounds of this type comprising recurring structural units of the following formulae:

 (A)

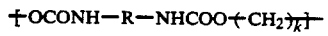 (B)

wherein L represents a hyperpolarizable group.

It will be appreciated that for a compound to exhibit square nonlinear optical activity, it is also necessary that it be well capable of being oriented under the influence of an electrical field and that it retain this orientation.

Materials exhibiting nonlinear optical activity are generally used in the form of films in optical or optoelectrical devices; these films must be as uniform as possible and have small thicknesses (a few tens of microns, $10^{-2}$ to $10^{-1}$ mm).

The materials described above present the additional major disadvantage of being weakly film-forming and poorly soluble in the solvents typically used to prepare films, such as dichloromethane, dimethylformamide (DMF), N-methylpyrrolidone (NMP), chloroform, cyclohexanone, methylisobutylketone.

SUMMARY OF THE INVENTION

Accordingly, a major object of this invention is the provision of novel nonlinear optically active organic polymer materials having good film-forming capability and a high solubility in conventional solvents, which novel polymers otherwise conspicuously avoid or ameliorate the above disadvantages and drawbacks to date characterizing the state of this art.

Another object of the present invention is the provision of characteristic monomers, the polymerization or copolymerization of which produces the above indicated polymers.

Briefly, the present invention features certain chemical species comprising at least two carbon-carbon double bonds, each such double bond being activated, i.e., the polymerization of which is facilitated by an electron attracting function, and further comprising a non-centrosymmetrical system of $\pi$ conjugated bonds bearing at least one electron attracting group on one of the terminals thereof and at least one electron donor group on the other terminal.

DETAILED DESCRIPTION OF THE PREFERRED EMBODIMENTS OF THE INVENTION

More particularly according to the present invention, such non-centrosymmetric system of $\pi$ conjugated bonds corresponds to different systems known to this art for their nonlinear square optical activity. Poorly polymerizable systems are preferred, the best known families of which are described herein, together with paradigms.

The electron attracting group may be an aromatic nucleus, a metalloid atom, advantageously nitrogen, oxygen or a halogen, preferably a chlorine atom; it may also be a carboxyl radical, a sulfone radical, etc. Too, it should be emphasized that there may be present several electron attracting functions to activate a double bond.

The electron attracting function is preferably selected from among functions derived from a carboxylic radical, such as, for example, the nitrile, ester, amide and, advantageously, the imide, preferably cyclic radicals and radicals comprising a cation, such as pyridinium salts.

The double bonds indicated are preferably essentially unhindered and are substituted on the carbons thereof, other than the aforementioned electron attracting functions, only with hydrogen atoms or substituents that are small in size, such as, for example, a chlorine atom or a methyl or ethyl radical.

Each of said double bonds is associated with the non-centrosymmetrical system of pi (π) conjugated bonds. This is advantageously effected by L links, which may be a simple valence bond or a hydrocarbon chain.

The L links are preferably such that there exists no interaction between said electron attracting function and said non-centrosymmetrical system of conjugated π bonds. The length of the links generally does not exceed 10 atoms and preferably ranges from 2 to 6 atoms.

The preferred links are advantageously aryls or alkyls as defined in M. C. Duval's Chemical Dictionary. The linkages include, for example, an aliphatic chain interrupted one or more times, optionally by a heteroatom, preferably a chalcogen or nitrogen, e.g., polyethylene diamine or polyethylene glycol. However, aryl or aralkyl links are the preferred.

Particularly exemplary such linkages include the following divalent radicals:

Cyclohexylene radicals; phenylenes, 4-methyl-1,3-phenylene, 2-methyl-1,3-phenylene, 5-methyl-1,3-phenylene, 6-methyl-1,3-phenylene, 2,5-diethyl-3-methyl-1,4-phenylene and radicals of the formula:

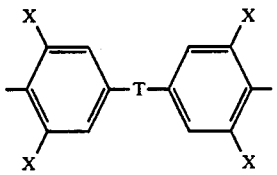

wherein T represents a simple valence bond or a group:

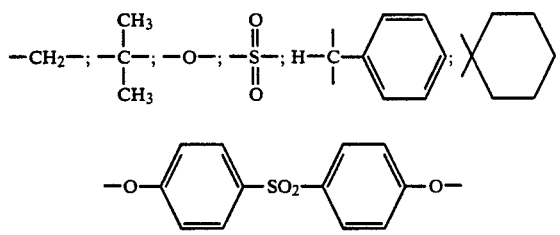

and X is a hydrogen atom, or a methyl, ethyl or isopropyl radical.

The points of attachment of said L links to said carbon-carbon double bonds are preferably such as to permit the opening of said double bond. Thus, a point of attachment on the side of said electron attracting function is preferably selected. For example, if said electron attracting function is selected from among derivatives of the carboxylic acid radical, such as, for example, the ester, amide and advantageously the imide radical, the bond is joined to this radical via the nitrogen or the oxygen.

The compounds according to the invention may be represented by the following formula:

Do—A—Do' wherein Do and Do', which are different but preferably similar, represent said activated double bond species, and A represents the system of (π) bonds comprising two similar or different L and L' linkages, such that A comprises a non-centrosymmetric system of π conjugated bonds and may be represented as

—L—A'—L'— with A' representing the π bond system.

Preferably, the compounds according to this invention correspond to the following formula:

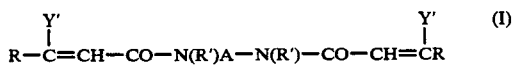

wherein the R radicals independently represent a hydrogen atom or alkyl or alkylidene radicals of low molecular weights ($C_1$ to $C_6$), or optionally substituted such radicals, with R and R' advantageously together forming a heterocycle having 5 to 7 atoms, wherein the symbols Y' independently represent H, $CH_3$ or Cl and A is as defined above.

Preferably, the R and R' radicals are selected such that the formula (I) is converted into formula (I'):

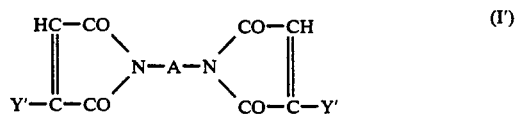

wherein the symbols Y' are as defined above; A represents a hyperpolarizable group advantageously having the formula:

$$E-Z_1-X-Y-Z_2-N$$

wherein X and Y independently represent N, C and/or CH; $Z_1$ and $Z_2$ are each an aromatic radical or an unsaturated divalent radical selected, for example, from among those derived from benzene (i.e., phenylene), pyridine, furan, styrene, acetylene, ethylene, etc.; and E represents an electron acceptor group.

Among the electron acceptor groups, the nitro and cyano radicals are the preferred.

In one embodiment of the invention, the aromatic radicals $Z_1$ and $Z_2$, which may bear at least one substituent $R_7$, are selected from among the phenyl, biphenyl and naphthyl radicals, with the $R_7$ radicals being independently selected from among the lower alkyl, halogen, amido, amino, sulfoxide, hydroxy, alkoxy and trifluoromethyl radicals.

The preferred such radicals are those that are intermediately unhindered, i.e., corresponding to the size of an isopropyl or isoamyl group.

If $R_7$ is situated on the $Z_1$ group, it is advantageously an electron donor, while if it is situated on $Z_2$, it is advantageously an electron acceptor. The $R_7$ radicals are advantageously in the ortho position relative to the —X=Y— chain.

Indeed, the presence of these radicals in the ortho position favors the conformation or transisomerism which permits the maximum elongation (or extension) of non-centrosymmetric systems. This maximum elongation is preferred.

Thus, one of the preferred family of compounds according to the invention is such that —$Z_1$—X=Y—$Z_2$— corresponds to the general formula:

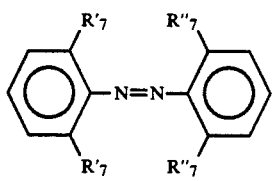

wherein $R'_7$ is selected from among the methyl, ethyl, isopropyl, propyl, isobutyl and butyl, $C_1$ to $C_4$ alkoxy and $C_1$ to $C_6$ amino radicals, and $R''_7$ is selected from among the methyl, ethyl, isopropyl, propyl, isobutyl, butyl and trifluoromethyl radicals, or chlorine or fluorine atoms, or amido or sulfoxide radicals.

By "lower alkyl radicals" are intended linear or branched alkyl radicals having 1 to 6 carbon atoms.

The preferred $R_7$ radicals according to the invention are the methyl, ethyl and chlorine radicals.

A' may be any nonlinear optically active organic radical such as described and exemplified in the article by H. E. Katz, C. W. Dirk, K. D. Singer and Te. Sohn, *Mol. Cryst. Liq. Cryst. Inc. Nonlin. Opt.*, 157, 525 (1988) and in the Rhône-Poulenc French applications 88/05,214, 88/12,028, 88/12,079, 88/12,080, 89/02,271, 89/04,232, 89/05,870, 89/10,196, 89/10,197, 90/00,377, 90/00,575, 90/02,336 and 90/05,420.

The present invention also features a process for the synthesis of useful monomer compounds.

As indicated above, the anchor point of the link on said bond system is of little importance, but it is preferable to utilize functions or radicals already existing in said bonding systems. Aniline or alkoxy radicals thus are well adopted for such anchoring.

Hence, if the synthesis with $\pi$ bonds entails an aniline function, which in general serves the function of a donor group, the anchoring point may then be the nitrogen atom, as it is easier to react alcohol radicals or alkyl graft radicals having an alcohol function. Thus, the replacement of a dimethylamino radical by a dihydroxyalkylamino radical provides a ready anchoring point.

If the $\pi$ bond system comprises an alkoxyphenol radical, the alkyl group can be readily replaced with a mono- or polyhydroxyalkyl radical. It is thus possible to replace the methyl radical with a $\omega,\omega$-dihydroxyalkyl radical. If the bond system comprises two alkylphenol radicals, it is sufficient to replace each of the alkyls by the respective links L and L'.

As the donor group generally preferred is a dimethylamino radical, the latter is replaced by a dihydroxyalkylamino radical, which makes possible the following reactions entailing alcoholic functions: reactions which, while per se known to this art, permit synthesis of the molecules according to the invention.

This list of reactions is not intended as exhaustive.

The synthesis of the monomers according to the invention may be carried according to conventional chemical techniques well known to this art. The most typical such techniques are indicated below.

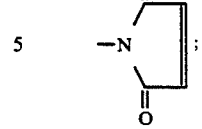

The maleimide radical is represented hereinafter by the abbreviation —Mal.

This reaction is generally represented as follows:

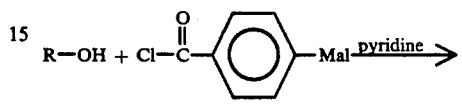

It is a conventional reaction; the HCl is scavenged by a base, for example pyridine.

For more complete details, see, for example, Rao et al, *Journal of Polymers*, 2510 (1989).

This is the simplest technique. The reaction proceeds with the necessary modifications in respect of the non-aromatic links:

$$R-OH + Cl-OC(CH_2)_{\overline{n}}Mal \longrightarrow$$

$$R-OC(CH_2)_{\overline{n}}Mal$$

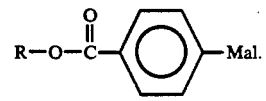

The following reaction is also appropriate:

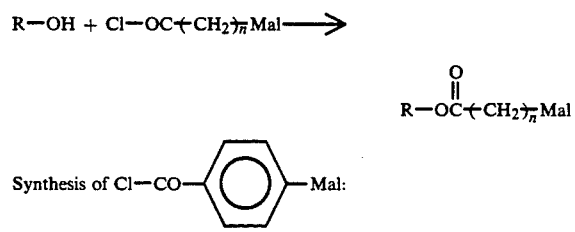

Grafting of other activated double bonds

Double bonds activated by an aromatic nucleus (styrene type):

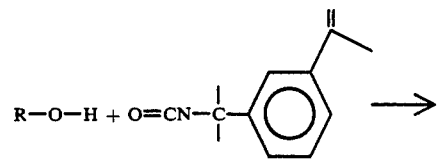

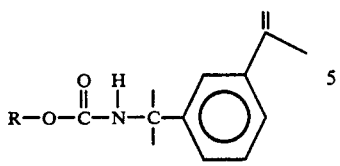

The isocyanate is marketed by American Cyanamid (TMI);

For the reaction of an alcohol with an isocyanate to produce urethanes (carbamates), see Satchell and Satchell, *Chem. Soc. Rev.*, 4, 231 (1975). Other available techniques:

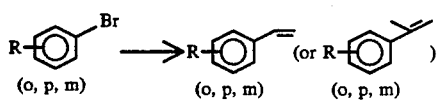

Heck reaction, Palladium 0 catalyst:

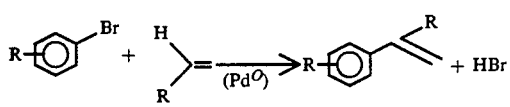

For a more detailed description of the Heck reaction, see Heck, *Org. Reactions*, 27, 345 (1982); Heck, *Ado. Catal.*, 26, 323 (1977); Jira, *Organometal. React.*, 3, C, 1-190 (1972).

Double bonds activated by a silicon atom:

Si Vinyl:

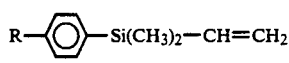

Grignard reaction:

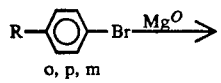

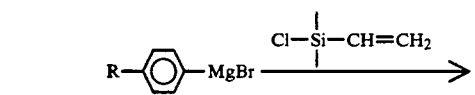

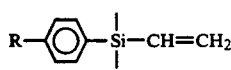

for example,

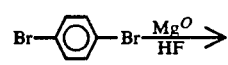

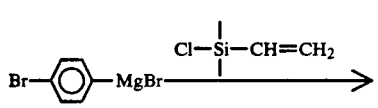

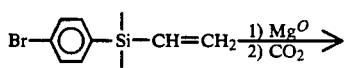

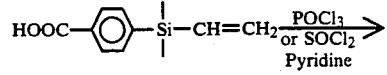

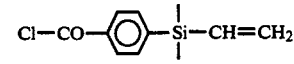

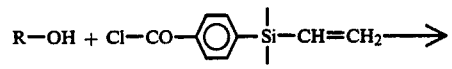

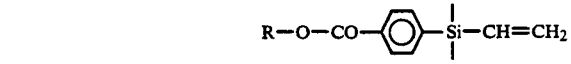

See, generally, "The chemistry of the carbonyl group", PATAI; GRIGNARD, Reaction of nonmetallic substances, KYARASCH & REINMUTH, Prentice-Hall, Englewood Cliffs (1954).

Double bonds activated by a nitrogen atom, for example:

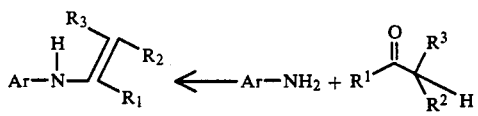

See SZMUSZKOVICZ, *Adv. Org. Chem.*, 4, 1-113 (1963). Double bonds activated by an oxygen atom, such as Enols:

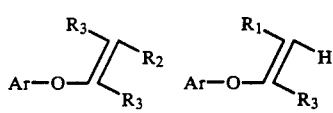

See *Advanced Organic Chemistry*, Third edition, Jerry March, J. Wiley & Sons (1985).

1. Provision of organosoluble precursors:

The "Red" colorants must have "diol" functions of the type:

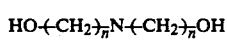

The most representative are compounds of the type:

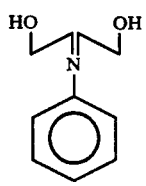

synthesized, for example:

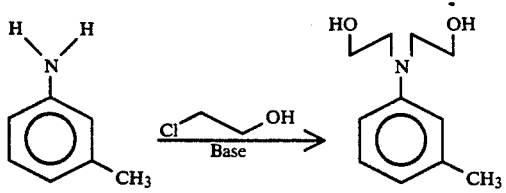

For further details, see W. Ross, *J. Chem. Soc.*, 183 (1949).

2. Provision of "Red" colorants of the diazo type:

In general, a conventional coupling reaction is employed, for example:

Synthesis of Red 17:

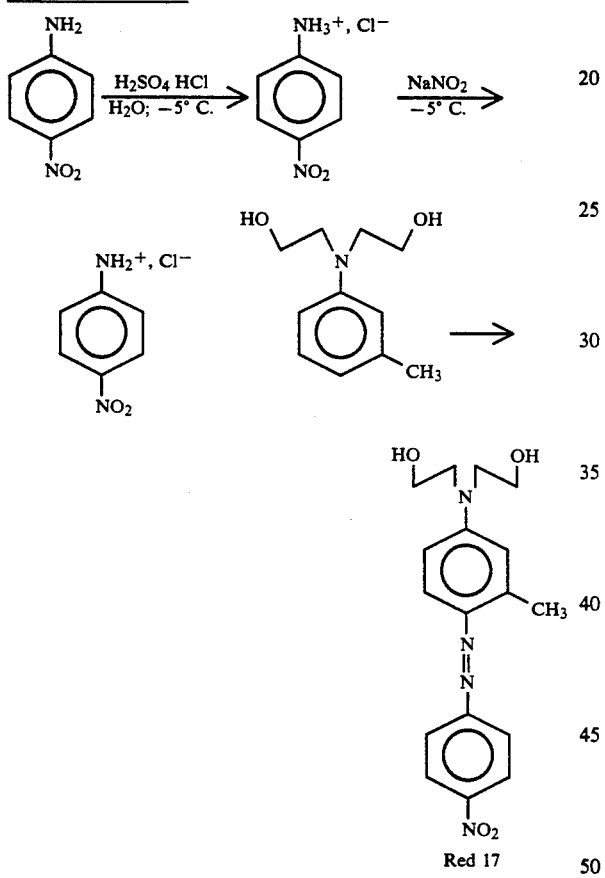

Red 17

Into a reactor, a dilute solution of a strong acid (of the HCl or H$_2$SO$_4$ type) is introduced, 50% W; one aniline equivalent is then added (for example:

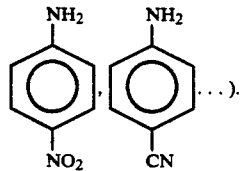

...).

After complete dissolution, the solution is cooled to −5° C. (with ice water) and subsequently one equivalent of NaNO$_2$ in a minimum of water is added. The diazo is allowed to form ($\frac{1}{2}$ hour to 1 hour). The coupler is then added, in general:

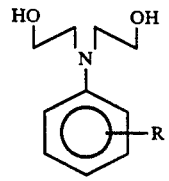

The mixture is permitted to react from 1 hour to 2 hours at ambient temperature. A precipitate is formed; the pH is then adjusted to 3 by addition of CH$_3$CO$_2$Na. The precipitate is filtered, washed with water (pH=1), dried in a vacuum, and recrystallized, if necessary (generally in alcohol). The diazo is recovered in a yield on the order of 70% to 95%.

The Red is purified by recrystallization (ethanol, methanol, etc.).

For additional details, see Zollinger, *Azo and Diazo Chemistry*, Interscience Publishers, Inc., New York (1961).

3. Provision of Red colorants of the stilbene type:

In U.S. Pat. No. 4,757,130, the following such stilbene is described:

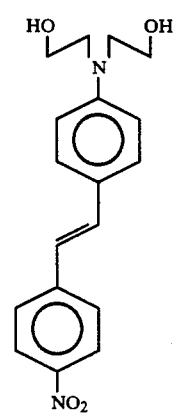

A compound of Type 1 may be prepared by a condensation reaction.

For further details, see K. Becker, "On the synthesis of stilbenes", *Synthese*, 341 (1943).

4. Provision of Red colorants of the alkyne type:

For example, U.S. Pat. No. 4,603,187 describes the compound:

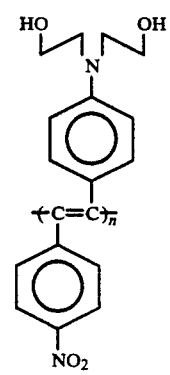

For operating details of the synthesis, see *Organic Synthesis*, Vol. III, 786 (1955); Vol. IV 857 (1963).

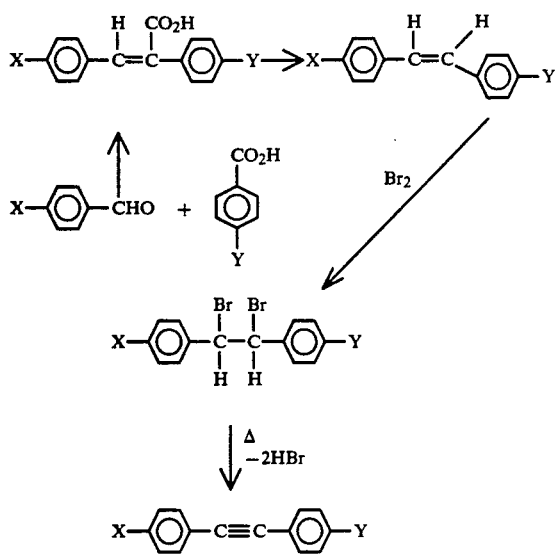

phenylene, 2-methyl-1,3-phenylene, 5-methyl-1,3-phenylene, 6-methyl-1,3-phenylene, 2,5-diethyl-3-methyl-1,4-phenylene, and the radicals of the formula:

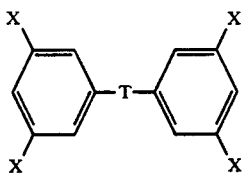

wherein T represents a simple valence bond or a group:

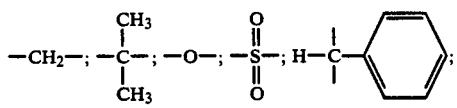

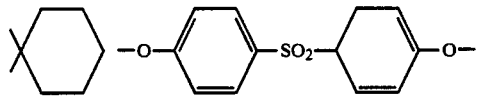

and X is a hydrogen atom, a methyl, ethyl or isopropyl radical;

one or more reagents (b) and/or (c):

(b) one or more heterocyclic compounds substituted, in particular, by unsaturated short chains ($C_2$–$C_6$), such as the vinylpyridines, N-vinyl-2-pyrrolidone, allyl isocyanurate, vinyltetrahydrofuran, etc., (c) a styrene type compound, such as, for example, α-methylstyrene, divinyl benzene or ethylvinyl benzene.

If it is desired that the reagent (b) or (c) be nonlinearly optically active, the substituted heterocycles or the styrene type compounds serve as the activated double bonds.

The present invention also features polymers prepared from the compounds described above.

Indeed, it has now surprisingly been found that the system of bonds is remarkably stable under the conditions of polymerization in the presence of activated double bonds, which polymerize them very rapidly. It is thus possible to provide a very broad wide of polymers according to the invention, the characteristic of which is the presence of at least one structural unit derived from the monomer compositions described above.

The (co)polymers according to the invention comprise at least 10%, advantageously at least ⅓ in moles, of the nonlinearly optically active monomer or monomers.

Such (co)polymers may also comprise various other conventional monomers that are not nonlinearly optically active.

Good results are provided by a formulation comprising:

(a) one or more N,N'-bisimide(s) of the formula:

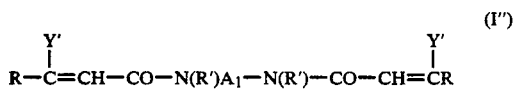 (I'')

wherein the radicals R independently represent a hydrogen atom or alkyl or alkylidene radicals of low molecular weight ($C_1$ to $C_6$), optionally substituted; R' independently represents an optionally substituted and/or unsaturated $C_1$–$C_6$ acylidene radical, with the proviso that R and R' may together form a heterocycle having from 5 to 7 atoms therein; wherein the symbols Y' independently represent H, $CH_3$ or Cl and $A_1$ is A as defined above or A'' as defined hereinbelow.

The radicals R and R' are preferably selected such that formula (I) is converted into the formula (I''').

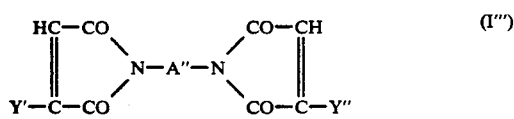 (I''')

wherein Y' and Y'' independently represent H, $CH_3$ or Cl; A'' is a divalent radical preferably selected from among the cyclohexylenes, phenylenes, 4-methyl-1,3-

The ratio (b+c)/a may vary from 1/20 to 10, preferably from 1/10 to 1, and, optionally, in order to improve the theology, one or more acrylate reagents (d) comprising one or more compounds of the formula:

$$(CH_2{=}CR_6{-}CO{-}O{\overline{)_n}}B \qquad (II)$$

wherein $R_6$ is a hydrogen atom or a methyl radical; n is an integer or fractional number at least equal to 1 and at most to 8; and B is an organic radical having a valence n derived from a saturated, linear or branched chain aliphatic radical having 1 to 30 carbon atoms, optionally containing one or more oxygen bridges and/or one or more free hydroxyl functions; from an aromatic radical (of arylic or arylaliphatic type) having 6 to 150 carbon atoms, comprising a benzene nucleus, optionally substituted by one or three alkyl radicals having 1 to 5 carbon atoms, or by several benzene nuclei optionally substituted, as indicated above, bonded together by a simple valence bond, an inert group or an alkylene radical having 1 to 3 carbon atoms, such aromatic radial optionally containing at different points in its structure one or more oxygen bridges and/or free hydroxyl functions, the free valence or valences of the aromatic radial B optionally borne by a carbon atom of an aliphatic chain and/or by a carbon atom of a benzene nucleus. The symbol B may also represent a radical A.

The quantity of the reagent is such that the weight ratio d/a may range from 0 to 1/10.

Optionally:

(e) one or more monomers of the formulae (III), (IV), (V):

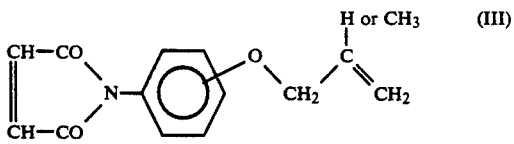

wherein the allyloxy or methallyloxy radical is in the ortho, metha or para position relative to the carbon atom of the benzene ring bonded to the nitrogen atom;

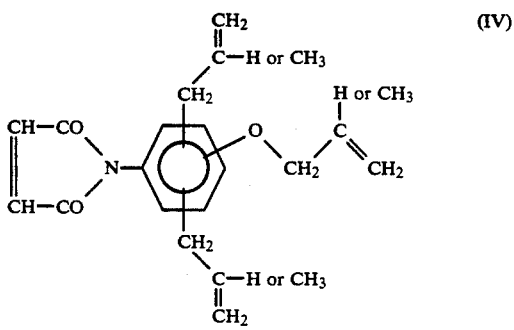

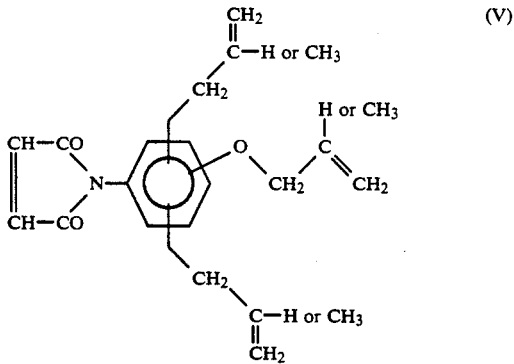

In the above compound, the proportions of the different components of the mixture of the products of formulae (III), (IV) and, optionally, (V), may vary over wide limits.

Each of the species a, b, c, d and/or e may be nonlinearly optically active, with the proviso that at least 5%, advantageously at least 10% and, preferably, at least ¼ of the total molar amount of such structural units is nonlinearly optically active.

Exemplary bisimides (a) that are not nonlinearly optically active and which have the formula (I″) are described in FR-86/17,918 and include:
N,N′-meta-phenylene-bismaleimide,
N,N′-para-phenylene-bismaleimide,
N,N′-4,4′-diphenylmethane-bismaleimide,
N,N′-4,4′-diphenylether-bismaleimide,
N,N′-4,4′-diphenylsulfone-bismaleimide,
N,N′-cyclohexylene-1,4-bismaleimide,
N,N′-diphenyl-1,1-cyclohexane-bis-maleimide,
N,N′-4,4′-diphenyl-1,1-cyclohexanebismaleimide,
N,N′-4,4′-diphenyl-2,2-propane--bismaleimide,
N,N′-4,4′-triphenylmethane-bismaleimide,
N,N′-2-methyl-1,3-phenylene-bismaleimide,
N,N′-2-methyl-1,3-phenylene-bismaleimide,
N,N′-4-methyl-1,3-phenylene-bismaleimide,
N,N′-5-methyl-1,3-phenylene-bismaleimide, These bismaleimides may be prepared by the processes described in U.S. Pat. No. 3,018,290 and GB-A-1,137,290. According to the present invention, N,N′-4,4′-diphenylmethane-bismaleimide is preferably used, whether alone or in admixture with N,N′-2-methyl-1,3-phenylene-bismaleimide, N,N′-4-methyl-1,3-phenylenebismaleimide and/or N,N′-5-methyl-1,3-phenylenebismaleimide.

Exemplary acrylate reagents (d) include the following:

(d1) the mono(meth)acrylates having the formula (II), wherein n is 1, B is a monovalent organic radical of the formula:

in which $B_1$ is a linear or branched chain alkyl radical having from 1 to 6 carbon atoms or a phenyl radical, and m is an integer equal to 0, or ranging from 1 to 9;

(d2) the di(meth)acrylates having the formula (IV) wherein n is 2, B is a divalent organic radical of the formula:

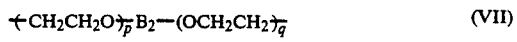

in which $B_2$ is a divalent, linear or branched chain alkylene radical having from 2 to 9 carbon atoms and optionally containing one or more oxygen bridges, or a radical of the formula:

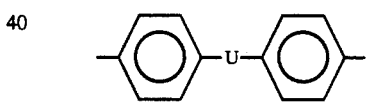

in which the symbol U is a simple valence bond or one of the groups:

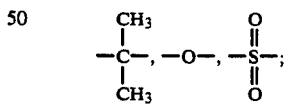

and the symbols p and q, which may be identical or different, are each an integer equal to zero, 1, 2, 3, 4 or 5;

(d3) the tri- and tetra(meth)acrylates having the formula (VI) wherein n is 3 or 4, and B is a trivalent or tetravalent organic radical derived from a saturated, linear or branched chain aliphatic radical having from 3 to 20 carbon atoms and optionally containing one or more oxygen bridges and/or one or more free hydroxyl functions;

(d4) epoxy novolak (meth)acrylates, which, while having the formula (IV), are here represented by the following formula:

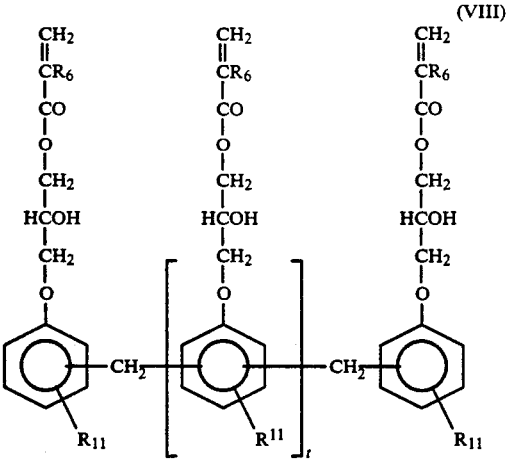
(VIII)

wherein $R_6$ is as defined above relative to formula (II), $R_{11}$ is a hydrogen atom or a methyl radical, and t is an integer or fractional number ranging from 0.1 and 7;

(d5) mixtures of a plurality of acrylates and/or methacrylates of the same type [(d1), (d2), (d3) or (d4)] or mixtures of one or more acrylates and/or methacrylates of the same type with one or more acrylates or methacrylates of another type; the constituents (a), (b), (c) or (d) may either be nonlinearly optically active or not, but the total amount of nonlinearly optically active constituents is at least equal to 10 molar %.

Particularly representative acrylate reagents (d1) include the methyl mono(meth) acrylates, the phenol(monooxyethyl)mono(meth)acrylates, and the phenol(dioxyethyl)mono(meth)acrylates.

Particularly representative acrylate reagents (d2) include the ethyleneglycol di(meth)acrylates, the 1,4-butanediol di(meth) acrylates, the 1,6-hexanediol di(meth)acrylates, the tripropyleneglycol di(meth)acrylates, the diphenol di(meth) acrylates or the di(mono- or polyoxyethyl) derivative, e.g., of 4,4'-dihydroxydiphenylmethane, bisphenol A, or 4,4'-dihydroxydiphenylether and in particular the di(meth)acrylates of (monooxyethyl)bisphenol A [compare formula (VII) in which $R_2$ is the radical:

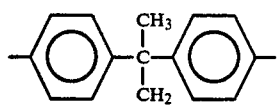

and p=q=1 or 2].

Particularly representative acrylate reagents (d3) include 1,2,4-butanetriol tri(meth) acrylate, 1,2,6-hexanetriol tri(meth)acrylates, trimethylolpropane tri(meth)acrylates, pentaerythritol tri(meth)acrylates, and pentaerythritol tetra(meth)acrylates.

The epoxy novolak (meth)acrylates (d4) are known polymers, certain of which are commercially available. They may be prepared by reacting (meth)acrylic acids with an epoxy resin of the novolak type, the latter being the product of the reaction of epichlorohydrin with the phenol/formol polycondensates of formula (VIII) given above and $R_{11}$ is then a hydrogen atom, or with the cresol/formol polycondensate and $R_{11}$ is then a methyl radical. These oligomer polyacrylates (d4) and a process for the preparation thereof are described, for example, in U.S. Pat. No. 3,535,403.

Particularly representative acrylate reagents (d4) include the epoxy novolak acrylates of formula (VIII), in which $R_6$ and $R_{11}$ are hydrogen atoms and t is an integer or fractional number ranging from 0.1 to 5.

Particularly representative acrylate reagents (d5) include mixtures of epoxy novolak (meth)acrylates with more than 30% by weight, relative to the mixture (d4)+(d3), of a triacrylate and/or a trimethacrylate as described above relative to the acrylate reagent (d3) and, in particular, the mixtures of the above epoxy novolak acrylates with a maximum of 25% by weight, relative to the weight of the mixture, of a triacrylate and/or a trimethacrylate selected from among those indicated above.

The acrylate reagent (d), which is very preferably included, comprises the di(monooxyethyl) bisphenol A di(meth) acrylates, the epoxy novolak di(meth)acrylates of formula (VIII) in which $R_6$ and $R_{11}$ are hydrogen atoms and t is an integer or fractional number ranging from 0.1 to 5; these compounds are used either alone or in admixture with a maximum of 25% by weight, relative to the weight of the mixture, of trimethylolpropane triacrylate.

The acrylate reagent (e) comprising one or more compounds of formula (IV) is used in amounts generrally constituting 1% to 60%, preferably 5% to 30% by weight of the total weight of the reagents (a)+(b) +optionally (c)+(d).

Advantageously, the aforesaid polymers have a viscosity in the molten state, measured under the conditions described below, ranging from 0.1 Pa.s to 500 Pa.s.

The polymerization may be carried out according to any technique known to this art, in particular via thermal process or by electron beam irradiation. If it is desired to produce films or any sheet material, it is preferable to first conduct a prepolymerization in order to provide prepolymers, the average number of monomers in which ranges from about 5 to about 100 (it is intended herein that the position zeros are not significant numbers).

This prepolymerization, which makes it possible to obtain a collodion, is advantageously carried out by a thermal process, preferably at a temperature ranging from 50° to 200° C., according to known technique.

After the material is shaped and polarization optionally carried out, polymerization is effected, advantageously cold, by irradiation preferably under the influence of an electron beam (with an exposure of from 1 to 50 M.Rad per μm of thickness under $1 \times 10^{21}$ electron volts/s). This technique is more fully described below.

The material according to the invention may be shaped into any form, such as films, molded shaped articles, extrusions, etc.

It is also possible according to the invention to incorporate different components or additives into such material to improve its mechanical or shaping properties, for example, flame retardants, antistatic agents, antioxidants, stabilizing agents, or the like.

The present invention also features optical or optoelectrical devices including at least one element comprising the material described above.

This invention also features a film-forming and orientable collodion. The polymers according to the invention display great capacity to be polarized and to maintain this polarization over time.

The polarization techniques, such as described herein, make it possible to provide a mean value of cos $\Theta$ ($<\cos\theta>$) generally ranging from $10^{-2}$ to 0.5, more generally ranging from 0.1 to 0.2. A tension of 20 to 25 v/$\mu$m yields approximately a cos $\theta$ of 0.1. In the zone in which $<\cos\theta>$ expands linearly as a function of the applied field, it is possible, by increasing the potential difference between the two face surfaces of the film, to enhance the orientation of the polymer by increasing the field to a value of about 100 volts/$\mu$m, a zone in which there is an inflection and the orientation ceases to expand proportionally with the field. It will be appreciated that $\theta$ is the angle formed by the orientation of the dipoles by the electrical field.

This polarization decreases very slowly over time in contrast to the other materials employed in nonlinear optics. It should be compared with the compound consisting of red 17 (10%) and poly(methyl methacrylate) (about 90%), the subject of the article by M. A. Montazani et al, *J. Opt. Soc. Am (B)*, Vol. 6, No. 4, page 733 (1989), wherein it is indicated that within one month 50% of the polarization has disappeared.

Furthermore, the presence of substituents in the aromatic moieties $Z_1$, $Z_1$ makes it possible to obtain materials having a maximum adsorption wave length ($\lambda$ max) at least equivalent to, but generally higher than that of the unsubstituted materials.

For film-forming and polarization purposes, the techniques briefly described hereinbelow are typically employed.

Formation of the film

Onto a glass plate coated with a conductive layer transparent at the wave length to be used, the collodion, the viscosity of which is adjusted to a value ranging from $\frac{1}{2}\times 10^{-2}$ to $\frac{1}{4}\times 10^3$, preferably from 50 to 200 centipoises, by the addition or evaporation of solvents, is formed into a film using a Mayer bar, employing a film drawing device such as, for example, the motorized apparatus marketed under the commercial designation of Erichson control coater. The film produced in this manner is dried gradually to a temperature closest to the glass transition temperature ($T_g$); the film is then dried in a vacuum to a temperature closest to the glass transition temperature for 24 hours.

When the film is dry, a second conductive layer is deposited and two electrodes are placed on the conducting layers. The conductive layers are either gold or different conducting oxides, such as tin oxide or the mixed oxides of tin and indium.

The thickness of the films according to the invention typically ranges from 0.1 to 100 $\mu$m, advantageously from 1 to 50 $\mu$m, preferably from 1 to 20 $\mu$m.

Polarization

Polarization is effected at a temperature at most equal to the final glass transition temperature and preferably close to the initial glass transition temperature. The polarizing voltage is applied between the two layers of gold. This voltage is selected between 1 and 200 volts per micrometer ($\mu$m). However, it is difficult and rare to attain the latter value, as the films have a tendency to crack under a strong potential difference, and that presently is the reason a voltage of from 10 to 100 volts per micrometer, typically from 20 to 30 v/$\mu$m, is selected.

When the polarization no longer varies significantly over time, cooling of the film, while maintaining a polarization voltage, is carried out. This polarization voltage may be slightly less than that of the initial polarization.

Quite surprisingly and unexpectedly, it has now been demonstrated that crosslinking can be thermally carried out, while at the same time preserving the polarization. This phenomenon is indeed surprising because, on the one hand, temperature increases electrical conductivity and thus limits the ability to support an intense electrical field and, on the other, the disorder or disorientation created by temperature is in opposition to the order induced by the field. According to the present invention, polymers are provided that can be polarized and thermally crosslinked without significant loss in cos $\theta$.

In a preferred embodiment of polarization in conjunction with thermal crosslinking, the film is subjected to an electrical field at a temperature of about the glass transition temperature and this temperature is increased up to that point in time when the orientation ceases to change. Once this value is attained, the temperature is maintained or increased above the glass transition temperature, which $T_g$ has itself increased by at most 20° C., advantageously 10° C. and preferably 5° C. It is also observed that the glass transition temperature is also increased, which permits increasing the temperature to which the film is subjected. The operation is carried out until the desired glass transition temperature is attained, typically 200° C. The loss in polarization over the course of time is remarkably reduced.

These materials are used, in particular, in optical or optoelectrical devices, such as, for example, switches, modulators, directional couplers, bistables, etc.

In order to further illustrate the present invention and the advantages thereof, the following specific examples are given, it being understood that same are intended only as illustrative and in nowise limitative.

From said examples to follow, it will be seen that the presence of substituents on the basic nucleus modifies the electronic structure of the molecule. It is thus possible to control and modify the maximum absorption wavelength ($\lambda$ max) of the polymer. For example, electron donating substituents, such as the alkyl radicals borne by the radical $Z_1$ make it possible to increase the $\lambda$ max, while halogens borne by the radical $Z_1$ reduce the $\lambda$ max (article by J. B. Dickey et al, *Am. Dyestuff Reporter*, page 44 (1965)).

When A' corresponds to the formula E—$Z_1$—X=Y—$Z_2$N, the presence of a substituent in the ortho position relative to the —X=Y— group, borne by the radical $Z_1$ and the radical $Z_2$, favors the trans configuration of the molecule. This configuration permits a better electronic dislocation in the molecule, thereby increasing its hyperpolarizability (article by S. Yamahamoto et al, *Bull. Chem. Soc. Japan*, 44, 2018 (1971) .

EXAMPLE 1

This example relates to the synthesis of a monomer suitable for the preparation of polymers of the bismaleimide type adopted for nonlinear optics applications.

The monomer was prepared according to the following process:

In 300 ml dimethylacetamide, under an inert nitrogen atmosphere, 15 g (64 mmole) p-maleimide-benzoic acid chloride (2) were dissolved with 1% NaI as the catalyst, and then 5 g (3) (16.4 mmole) and 34 mmole tributylamine were added. The mixture was agitated and heated to 40°-45° C. for about 12 hours. The solution was then filtered and precipitated in 1,000 ml water. The solids were washed with water, then dried in a vacuum for 12 hours at ambient temperature. It was chromatographed on silica, with dichloromethane and then a 1/1 by volume mixture of dichloromethane/ethyl acetate as the eluent.

The red/orange fraction was recovered and dried: 8.5 g of red solids (yield 70%) were obtained.

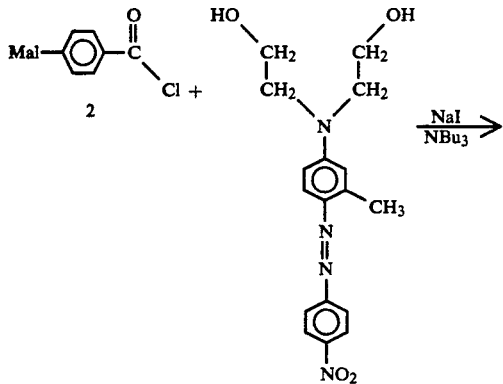

2

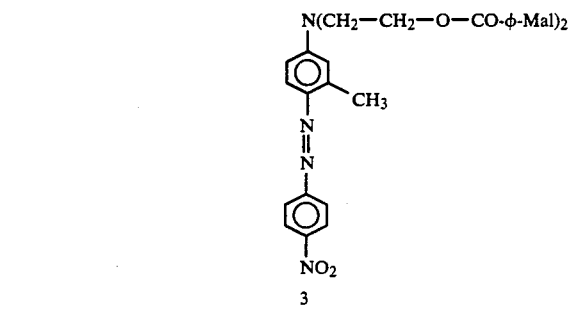

3

The spectroscopic data (NMR, mass spectroscopy) confirmed the structure proposed.

EXAMPLE 2

A mixture (85% by weight N-vinylpyrrolidone; 15% by weight of compound 1).

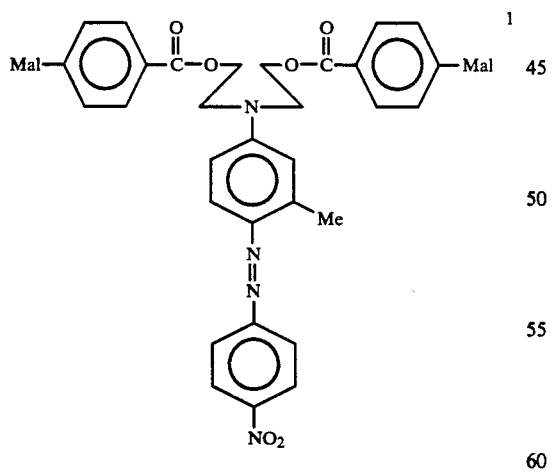

1 was heated to 120° C. over a varying period of time (15 min to 120 min). The degree of the progress of the polymerization varied with the heating time. The $T_g$ of the films, prepared on the film drawer from collodions, was also modified. The $T_g$ measured at 50 Hz by the variation of the dielectric constant of the film as a function of temperature, ranged from 90° to 150° (for a collodion, 30 min at 120° C. and 180 min at 120° C.) at $T > T_g$. The films produced were polarized by applying a dc field of about 20 V/μm. After polarization, the film was cooled to ambient temperature while maintaining a field such that:

(E polarization)/T = constant

The films produced were crosslinked, thereby increasing the $T_g$ by irradiation under an electron beam (16 MRad under a curtain electron beam).

Thus, for a film, the $T_g$ of which was 140° C. (prepolymerization of 120 mint 120° C.) prior to radiation, it changed to 190° C. after irradiation.

Therefore, the electro-optical activity, measured by the PFOI method [R. Meyrueix, G. Mignani, G. Tapolsky, SPIE, Vol. 1127, 160 (1989)], of these films, polarized and crosslinked under the influence of an electron beam, was constant within the limits of detection for a period of 2 months.

EXAMPLE 3

Synthesis of:

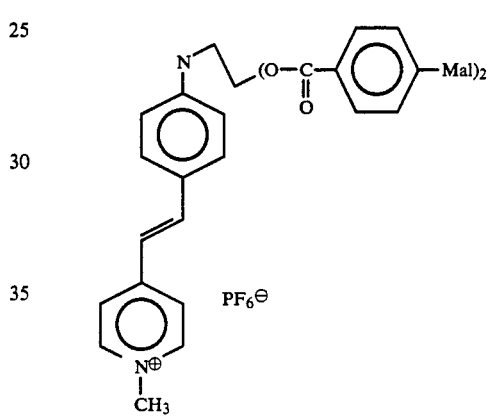

Into a two-liter three-necked flask were introduced

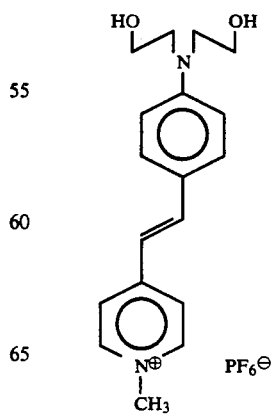

81.3 g (0.345 moles), 800 ml dimethylacetamide anhydride (DMAC), 51.5 G (0.16 mole) of 2.5 g (0.0167 mole) NaI and 53 g tributylamine, and these were reacted for 3 hours at ambient temperature and 16 hours at 40° C. The mixture was precipitated in 6 l water. An orange precipitate was formed. It was filtered, abundantly rinsed with water to eliminate the

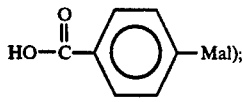

the precipitate was dried under vacuum and 98 g of an orange solid were formed. By means of chromatography on a silica gel column (eluent=acetone/hexane//75/25/V/V/)+1 ml of a solution of $NH_4PF_6.H_2O$ per liter of eluent.

9 g of an orange solid were recovered; melting temperature 95° C. (decomposition); isolated yield: 10.2%.

IR, UV, $^1HNMR$ and mass spectrum analyses confirmed the structure of the product.

Preparation of the collodion/film forming

The collodion was prepared in NVP (N-vinylpyrrolidone) in a weight concentration of active molecule/NVP=85/15. This collodion was heated to 120° C. in 1 hour; the collodion prepared in this manner was filtered on a 0.2 μm filter, then formed into a film by conventional methods (film drawing, Mayer bar).

Polarization and crosslinking:

The techniques were identical to those of Example 1.

EXAMPLE 4

Synthesis of polymer B

The procedure was according to the technique of B. Kovacic, J. Org. Chem., 1187 (1959). In a flask containing 250 ml DMAC anhydride, 860 mg of the monomer A (1,168 mole) were dissolved. To this solution, a stoichiometric amount of N,N'-diethylhexamethylenediamine was added. The solution was heated to 110° C. under nitrogen over 48 hours. When the temperature of the solution decreased to ambient, it was precipitated in water. A red precipitate was recovered and was washed with water. It was then dried in a vacuum for 12 hours. 900 mg of polymer were obtained, the glass transition temperature (Differential Scanning and Colometrie, Perkin-Elmer DSC) of which was 77°±2° C. and the structure of which, set forth below, was confirmed by spectroscopic, NMR and IR analyses.

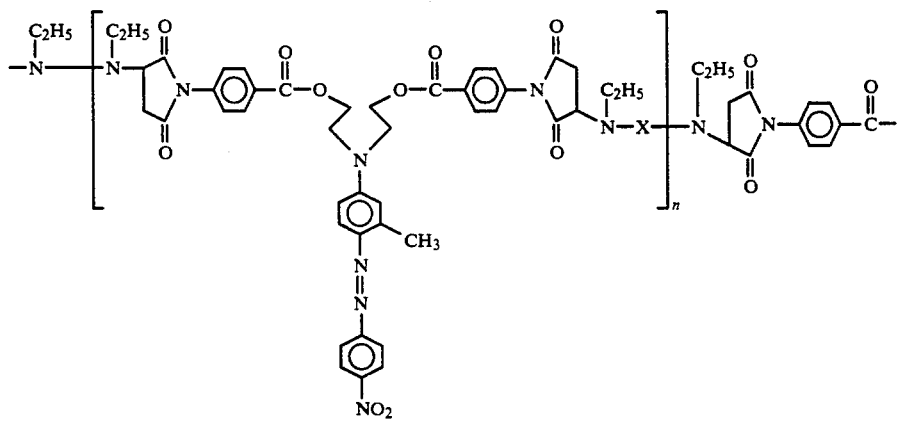

The glass transition temperature of the polymer B could be modified by using different diamines and aromatic compounds, as descried in Examples 5 and 6.

EXAMPLE 5

Synthesis of polymer C

Following the procedure of Example 4, 517 mg (0.7 mmole) of A were dissolved in 20 ml DMAC and 43 mg (0.7 mole) ethylenediamine were added. After 48 hours at 110° C., the polymer was precipitated in methanol and the precipitate dried in a vacuum. The glass transition temperature of the polymer was 107°±2° C.; its structure is set forth below and was confirmed by NMR and IR.

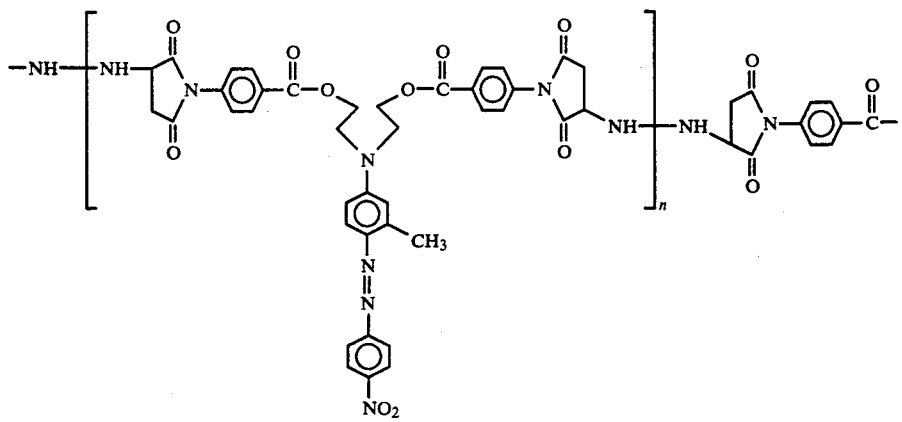

EXAMPLE 6

Synthesis of polymer D

This synthesis was identical to that of the preceding example, except that para-phenylene diamine was used. In 25 ml DMAC, 0.8 mmole of p-phenylene diamine was dissolved. 25 mg benzoyl peroxide were added as the polymerization catalyst. After 24 hours at 110° C., the solution was precipitated in water and a red precipitate was obtained, the structure of which is set forth below and was confirmed by NMR and IR analysis; its glass transition temperature was 145°C.±2° C.

EXAMPLE 7

Synthesis of polymer E

The procedure was according to the technique of R. Bacskaj, J. Pol. Sci., A (10), 1297 (1972). 736 mg (1 mole) of the monomer A were dissolved in freshly distilled THP. Two equivalents, 145 mg, of ethylvinylether and 50 mg benzoyl peroxide were added. The solution was heated to reflux under nitrogen. After 24 hours the solution was permitted to cool to ambient temperature and was then precipitated in methanol. A red precipitate was recovered and was washed and dried in vacuum. The structure of the polymer set forth below was confirmed by spectroscopic, NMR and IR analyses. Its glass transition temperature was 120°±2° C.

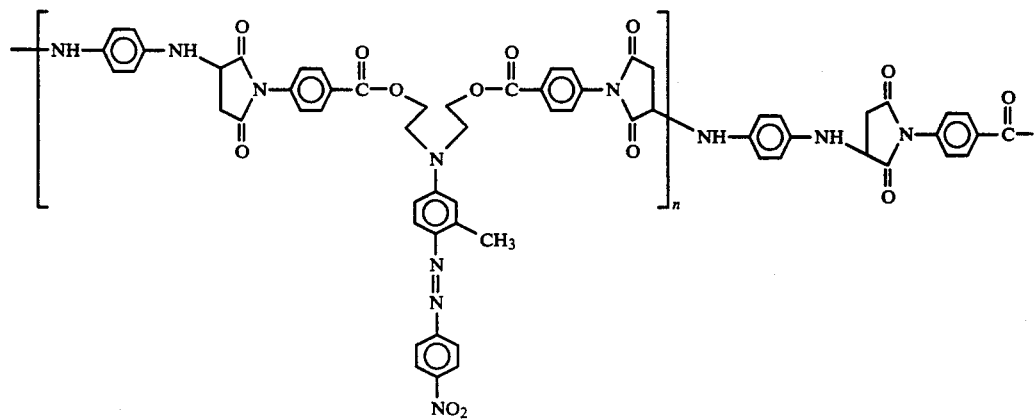

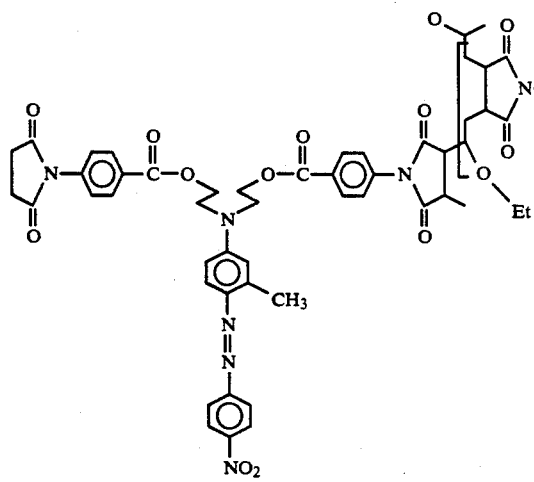
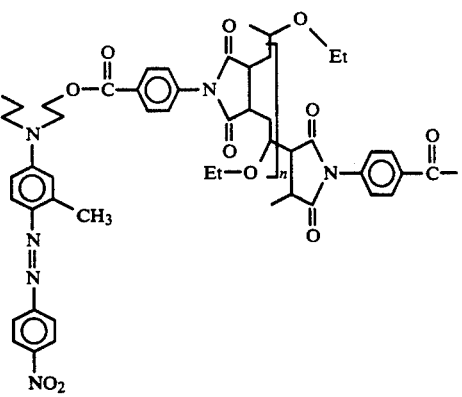

As described in Example 2, it was possible to prepare films of these polymers and to post-crosslink the films utilizing techniques well known to this art, such as photocrosslinking, crosslinking by electron beam irradiation or thermal crosslinking.

EXAMPLE 8

Synthesis of polymer F

The synthesis was identical to that described in Example 5, except that 0.7 mmole of the monomer A and 0.45 mmole ethylene diamine were used. The polymer obtained had a glass transition temperature of 103°±2° C. A solution of this polymer in DMAC may be formed into a film by the conventional techniques described above. The film was then crosslinked under an electron beam by the method described in Example 2. The glass transition temperature of the film after crosslinking was 140°±2° C. It was also possible to shape film from a solution of this polymer and N-vinylpyrrolidone and irradiate the film thus obtained. The glass transition temperature was then 147°±2° C.

EXAMPLE 9

Synthesis of polymer G

This synthesis was identical to that of Example 7, except that a different molar ratio was employed. For 736 mg of monomer, 0.65 mmole ethylvinyl ether was added. The polymer obtained had a glass transition temperature of 109°±2° C. A solution of this polymer in DMAC and containing N-vinylpyrrolidone was formed into a film. The film was crosslinked under an electron beam by the technique described in Example 2. The glass transition temperature of the film was then 175° C.

The films may also be crosslinked under electron beams as described in Examples 8 and 9. It too is possible to photo-crosslink the films by means of a suitable photoinitiator, as is well known to this art.

EXAMPLE 10

Synthesis of Polymer H

This synthesis was identical to that of Example 6, except that 0.7 mmol of mortmet A and 0.45 mmol of para-ethylene diamine were used. The polymer obtained had a glass transition temperature of 113°±2° C. A film was formed from a solution of this polymer in the DMAC by the technique described above. This film was then crosslinked by electron beam irradiation according to the procedure described in Example 2.

The film could also be crosslinked thermally. A film was shaped from a collodion containing N-vinylpyrrolidone (10% by weight). The film was polarized and simultaneously thermally crosslinked, as described above relative to the polarization stage, to provide a glass transition temperature of at least 180° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A nonlinearly optically active monomer species comprising at least two carbon-carbon activated double bonds and a non-centrosymmetric system of pi ($\pi$) conjugated bonds bearing at least one electron attracting group on one terminal thereof and at least one electron donor group on the other terminal, wherein the monomer species has the formula (I):

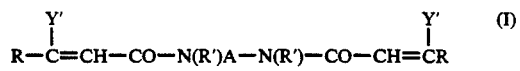

wherein R is a hydrogen atom or a lower alkyl or alkylidene radical; R' is a lower acyl or acylidene radical, or R and R' when taken together form a heterocycle having from 5 to 7 atoms; and A comprises said non-centrosymmetric system of $\pi$ conjugated bonds and wherein Y' is H, CH$_3$ or Cl.

2. The monomer species as defined by claim 1, having the formula (I'):

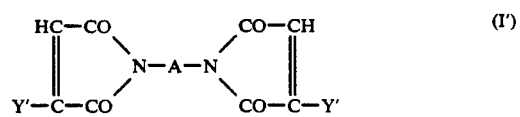

wherein Y' is H, CH$_3$ or Cl.

3. The monomer species as defined by claim 1, wherein A has the formula —L—A'—L'—, in which L and L' are linking moieties and A' comprises said noncentrosymmetric system of $\pi$ conjugated bonds.

4. The monomer species as defined by claim 3, wherein A' is a hyperpolarizable group.

5. The monomer species as defined by claim 4, wherein A' has the formula:

$$E-Z_1-X=Y-Z_2-N<$$

in which X and Y are N, C or CH; $Z_1$ and $Z_2$ are unsaturated or aromatic divalent radicals; and E is an electron acceptor group.

6. The monomer species as defined by claim 5, in which $Z_1$ and $Z_2$ are divalent benzene, pyridine, furan, styrene, alkyne or alkene radicals.

7. The monomer species as defined by claim 6, in which E is a nitro or cyano radical.

8. The monomer species as defined by claim 4, wherein $-Z_1-X=Y-Z_2-$ has the formula:

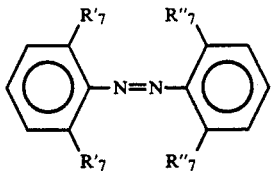

in which $R'_7$ is a lower alkyl, lower alkoxy or lower alkyl amino radical, and $R''_7$ is a lower alkyl trifluoromethyl, halo, amido or sulfoxide radical.

* * * * *